US006545006B1

(12) United States Patent
Milbert et al.

(10) Patent No.: US 6,545,006 B1
(45) Date of Patent: Apr. 8, 2003

(54) PROCESS FOR OBTAINING L-DIHYDROOROTIC ACID AND USE THEREOF

(75) Inventors: Ulrike Milbert, Idstein (DE); Robert Bartlett, deceased, late of Darmstadt (DE), by Krista Margit Bartlett, Germaine Belinda Bartlett, heirs; Eric Ruuth, Boulogne (FR); Claude Fudali, Senlis (FR)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/581,142

(22) PCT Filed: Dec. 8, 1998

(86) PCT No.: PCT/EP98/07972

§ 371 (c)(1),
(2), (4) Date: Dec. 11, 2000

(87) PCT Pub. No.: WO99/30146

PCT Pub. Date: Jun. 17, 1999

(30) Foreign Application Priority Data

Dec. 11, 1997 (EP) ............................................ 97121848

(51) Int. Cl.[7] ...................... A61K 31/505; C07D 239/02

(52) U.S. Cl. ............................. 514/269; 435/4; 435/26; 435/183; 435/220; 514/49; 514/270; 544/300

(58) Field of Search ............................... 435/26, 4, 183; 435/220; 514/49, 269, 270; 544/300

(56) References Cited

U.S. PATENT DOCUMENTS

| | | | |
|---|---|---|---|
| 2,773,872 A | 12/1956 | Miller et al. | |
| 5,886,033 A | 3/1999 | Schwab et al. | |
| 6,020,372 A | 2/2000 | Schwab et al. | |

FOREIGN PATENT DOCUMENTS

| | | | |
|---|---|---|---|
| DE | AT 360040 | * 12/1980 | |
| EP | 0 769 296 A1 | 4/1997 | |

OTHER PUBLICATIONS

Peters et al. "A sensitive, nonradiometric assay for dihydroorotic acid dehydrogenase using anion–exchange high–performance liquid chromatography." Abstract: Anal. Biochem. (1987), 161(1), 32–38.*
Abstract: EP 0 769 296 A1 (Derwent Abstract No. 97–228466).
Christopherson, Richard I.; Matsuura, Takao; and Jones, Mary Ellen, "Radioassay of Dihydroorotase Utilizing Ion–Exchange Chromatography," *Analytical Biochemisry*, vol. 89, pp. 225–234 (1978); and corresponding Chemical Abstract No. 89:159221.

Daniel, R.; Kokel, B.; Caminade, E.; Martel, A.; and Le Goffic, F., "Assay of *Escherichia coli* Dihydroorotase with Enantimoeric Substrate: Practical Preparation of Carbamyl L–Aspartate and High–Performance Liquid Chromatography Analysis of Catalysis Product," *Analytical Biochemisry*, vol. 239, pp. 130–135 (1996); and corresponding Chemical Abstract No. 125:188973.
Herrmann, E. Clifford; Dunn, John H.; and Schmidt, Robert R., "DEAE Paper Chromatography to Separate Intermediates of the Pyrimidine Biosynthetic Pathway and to Assay Aspartate Transcarbamylase and Dihydroorotase Activities," *Analytical Biochemistry*, vol. 53, pp. 478–483 (1973); and corresponding Chemical Abstract No. 78:155812.
Hisata, Toshikazu and Tatibana, Masamiti, "Control of de novo Pyrimidine Biosynthesis in Mammalian Tissues Levels and Turnover of Early Intermediates in Mouse Spleen in vivo," *Eur. J. Biochem.*, vol. 105, pp. 155–161(1980); and corresponding Chemical Abstract No. 92:178041.
International Search Report, dated Apr. 8, 1999; and Partial European Search Report, dated Jun. 9, 1998.
Ittarat, Isra; Webster, H. Kyle; and Yuthavong, Yongyuth, "High–performance liquid chromatographic determination of dihydroorotate and dehydrogenase of *Plasmodium falicparum* and effects of antimalarials on enzyme activity," *Journal of Chromatography*, vol. 582, pp. 57–64 (1992); and corresponding Chemical Abstract No. 118:150.
Kensler, Thomas W.; Han, Nyun; and Cooney, David A., "A Straightforward Method for the Simultaneous Preparation of Radiolabeled L–Dihydroörotic and N–Carbamyl–L–Aspartic Acids," *Analytical Biochemistry*, vol. 111, pp. 49–53 (1981); and corresponding Chemical Abstract No. 94:188058.
Kesner, Leo; Aronson, Frank L.; Silverman, Morris; and Chan, Phillip C., "Determination of Orotic and Dihydroorotic Acids in Biological Fluids and Tissues," *Clin. Chem.*, vol. 21, No. 3, pp. 353–355 (1975); and corresponding Chemical Abstract No. 83:4139.
Mehdi, Shujaath and Wiseman, Jeffrey S., "An Assay for Dihydroorotase Using High–Performance Liquid Chromatography with Radioactivity Detection," *Analytical Biochemistry*, vol. 176, pp. 105–108 (1989); and corresponding Chemical Abstract No. 110:130922.
Peter, G. J.; Laurensse; Leyva, A.; and Pinedo, H. M., "A Sensitive, Nonradiometric Assay for Dihydroorotic Acid Dehydrogenase Using Anion–Exchange High–Performance Liquid Chromatography," *Analytical Biochemistry*, vol. 161, pp. 32–38 (1987); and corresponding Chemical Abstract No. 106:209829.

* cited by examiner

*Primary Examiner*—Samuel Barts
*Assistant Examiner*—Devesh Khara
(74) *Attorney, Agent, or Firm*—Irving Newman

(57) ABSTRACT

The invention relates to a process for obtaining L-dihydroorotic acid by chromatography on an anionic exchange material in a base water mixture under a pressure from about 1.1 MPa to about 40 MPa. The process can be used to investigate the in vitro and in vivo activity of N-(4-trifluoromethylphenyl)-5-methylisoxazole-4-carboxamide, N-(4-trifluoromethylphenyl)-2-cyano-3-hydroxycrontonamide and similar compounds.

13 Claims, No Drawings

PROCESS FOR OBTAINING L-DIHYDROOROTIC ACID AND USE THEREOF

This application is filed under 35 U.S.C. §371, and claims the benefit of the filing date under 35 U.S.C. §119(a) for European Patent application serial no. EP 97121848.2, filed on Dec. 11, 1997, and claims the benefit of the filing date under 35 U.S.C. §365 for PCT international application number PCT/EP98/07972, filed on Dec. 8, 1998.

The invention relates to a process for obtaining L-dihydroorotic acid (in the following "L-DHO") by chromatography on an anionic exchange material in a base water mixture under a pressure from about 1.1 MPa to about 40 MPa. The process can be used to investigate the in vitro and in vivo activity of N-(4-trifluoromethylphenyl)-5-methylisoxazole-4-carboxamide, N-(4-trifluoromethylphenyl)-2-cyano-3-hydroxycrontonamide and similar compounds.

L-DHO can be determined by a silica gel chromatographic procedure with subsequent chemical derivatisation and colorimetric determination (Kesner, L., Aronson, F. L., Silverman, M., Chan, P. C., Clin. Chem 21/3 (1975) 353). Another method converts L-DHO enzymatically to orotic acid by L-dihydroorotic acid dehydrogenase (in the following "DHODH") prepared from rat liver and, after chemical derivatization, detects orotate by colorimetric changes (Rogers, L. E., Nicolaisen, K., Experientia 28/10 (1972) 1259). The disadvantages of these methods are the interference of other materials in complex physiological solutions. In addition the mentioned procedures are very time consuming because of laborious sample preparation and therefore not applicable for routine analysis in large clinical studies.

In the endeavor to provide improved separation and isolation processes for obtaining L-dihydroorotic acid, it has now been found that the same can be achieved by chromatography of L-DHO in a base water mixture on an anionic exchange material and a pressure of about 1.1 MPa to about 40 MPa. The process can be used for the quantitative determination of L-DHO in cell lysates, mammalian serum and human serum. Said process is highly reproducible, sensitive and validated.

The invention, as it is explained in the claims, achieves the object by a chromatography process comprising the steps of:
a) obtaining a column comprising pressure-stable anionic exchange material;
b) loading the column with a sample solution including L-dihydroorotic acid;
c) performing chromatography;
d) eluting the L-dihydroorotic acid with an eluting solution containing a base water mixture;
said process being performed under a pressure from about 1.1 MPa to about 40 MPa.

The term pressure-stable anionic exchange material means, for example, materials such as macroporous (2,000 Å) divinylbenzene/ethylvinylbenzene polymer or a microporous polyvinylbenzylammonium polymer cross-linked with divinylbenzene or mixtures thereof which are modified with alkanol quaternary ammonium; or vinylbenzylchloride/divinylbenzene macroporous polymer; or crosslinked Polyethyliminopolymer; or silica modified with propyl-trimethyl-ammonium; or poly(styrene-divinylbenzene)trimethylammonium. The following products are particularly preferred:

Ion Pac AS 11, CarboPac PA 1 or CarboPac MA 1 anion exchange columns supplied by Dionex Corporation, Idstein, Germany, GROM-SIL, Strong Anion. or GROM-SIL, Weak Anion.; supplied by Grom P1000 SAX, Ionospher SA or Chrompack PA; supplied by Chrompack PRP-X100 or RCX-10 supplied by Hamilton The election solution contains a base water mixture. Suitable bases are derived from alkali metals or alkaline earth metals, such as sodium hydroxide, potassium hydroxide, magnesium hydroxide or calcium hydroxide. The concentration of the base is from 1 mmol/l to about 200 mmol/l, based on water as solvent, preferably from 2 mmol/l to about 120 mmol/l, particularly preferred is 100 mmol/l. The temperature during the chromatography procedure is from about 0° C. to about 50° C., preferably from about 15° C. to about 30° C., particularly preferred from about 19° C. to about 25° C. The operating pressure during the chromatography is substantially constant. The chromatography can be carried out using different pressures, for example the chromatography can be carried out under a pressure from about $1.1 \cdot 10^6$ Pa (1.1 MPa) to about $40 \cdot 10^6$ Pa (40 MPa), in particular from 4.1 MPa to 5.5 MPa. The eluent flow rates are from about 0.2 ml/min to about 3 ml/min, preferably 1 ml/min. The loading of the columns, chromatography, and elution of the L-DHO takes place by known, conventional technical methods. A suitable elution is one in which the elution displays a time gradient of the base concentration, preferably with a linear course. This concentration gradient can be applied, for example, by a low base concentration (zero in the limiting case) being present in the elution at the start of the elution, and by increasing the base concentration during the elution process. It is possible in this way to achieve a particularly effective separation of the L-DHO in samples derived from serum or cell lysates. A preferred base gradient varies from near 1% NaOH (100 mmol/l) and 99% water (at the start of the elution) to about 60% NaOH and 40% water (at the end of the elution), with the particular preferable range being from about 1% NaOH and 99% water (at the start of the elution) to about 15% NaOH and 75% water (at the end of the elution). The base water gradient is changed in a linear way from 2.5 min to about 14 min and from 14 min to about 25 min, wherein the steep of the gradient is different during these 2 time periods.

A particularly suitable elution can be achieved by using a low base concentration at the start of the separation process of about 1% for a time period of about 2.5 minutes. The result is eluting most of the interfering material from the biological matrix from the column. The separation of the analyte is achieved by slowly increasing the gradient to about 23% of base within a time period of a 14 minutes total analysis time. Then the base cncentration is incresed to about 60% within 4 min to allow the elution of strongly bond material. 60% base should be applied for no longer than 6 min until reequilibration is performed by 1% base water mixture. The next analysis is started after 45 min of total analysis time. The water in the base water gradient has to be deionized and degassed.

The separation process according to the invention takes place in a column process. The temperature, which is preferably kept constant during the anionic exchange chromatography, may be varied within a wide range. A preferred temperature range is from about −10° C. to about 50° C., in particular from about 15° C. to about 25° C.

The elution of L-DHO takes place from 10 min to 12 min after start of the gradient. The running time of the elution process is from 13 min to 25 min. The L-DHO is detected by a conductivity detector, such as model CD20 from Dionex Cooperation. In order to minimize the base line shift and to lower the background conductivity an anion self regeneration suppresser, such as model ASRS-I, 4 mm from Dionex Cooperation, can be used.

The process according to the invention is in particular suitable for analytical chromatography but can also be used for preparative chromatography, especially when the process according to the invention is carried out with a preparative high pressure liquid chromatography column (HPLC) system. The term "preparative chromatography" means a purification process with the aim of obtaining, and not merely analyzing, pure products. The amount of the pure products can vary within wide limits, for example from 1 mg to 1000 g, preferably between 50 mg and 500 mg.

The process according to the invention can be used to detect changes in intracellular or extracellular L-DHO concentrations due to the inhibition of dihydroorotic acid dehydrogenase (DHO-DH). The enzyme DHO-DH is responsible for the conversion of L-dihydroorotic acid to orotic acid during the de novo pyrimidine synthesis. The inhibition of DHO-DH leads to the accumulation of L-DHO. The process according to the invention can be used for the preparation of a diagnostic assay. The process according to the invention can be used for determining the activity of DHO-DH inhibitors. DHO-DH inhibitors are for example N-4-(trifluoromethylphenyl)-5-methylisoxazol4-carboxylamide, Brequinar, N-(4-(trifluoromethylphenyl)-2-cyano-3-hydroxyhept-2-en-6-yne-carboxamide, 2-cyano-3-cyclopropyl-3-hydroxyacrylic-acid-(4-cyanophenyl)-amide or N-(4-trifluoromethylphenyl)-2-cyano-3-hydroxycrotonamide. The process according to the invention can be used for determining L-DHO concentrations in plants, cell lines, animals and human beings. L-DHO determination can be used to monitor the activity of DHO-DH inhibitors in plants, mammals and human beings.

The process according to the invention is described in detail in the examples which follow. Unless otherwise indicated, percentage data relate to weight.

EXAMPLE 1

1.1. Chemicals and Reagents

Chemicals and reagents were purchased as indicated below:

| | |
|---|---|
| Carbonate free NaOH and KOH | Baker, Holland |
| L-Dihydroorotic Acid (L-DHO) | Sigma, Munich |
| HClO$_4$ | Riedel de Haen, Seelze |
| Eosin, Chloroform | Riedel de Haen, Seelze |
| RPMI 1640 medium | Gibco, Eggenstein |
| Fetal calf serum (FCS) | Bio Whitaker, Verviers, Belgium |

Deionized water had to be degassed by helium prior to use.

1.2. Chromatographic Equipment

The HPLC system consisted of the following instruments:

| Equipment | Model | Producer |
|---|---|---|
| Solvent conditioning module | SCM 400 | Thermo separation products (TSP) |
| Binary gradient pump | P 2000 | TSP |
| Autosampler with 20 μl loop | AS 3000 | TSP |
| Interface | SP 4510 | TSP |
| AD changer | SN 4000 | TSP |
| Conductivity detector | CD 20 | Dionex |
| Anion self regenerating suppresser | ASRS-I 4 mm | Dionex |
| Detection stabilizer | DS 3-1 | Dionex |
| PC | EI 20, Flex Scan, F 563-T | Escon |
| Printer | Desk Jet 550 C | Escon |
| software | PC 1000 | TSP |

Peek material was used throughout the experiments 1.3. HPLC Conditions

The chromatographic separation was performed with a 250×4 mm I.D. IonPac AS 11 anion exchange column (particle size 13 μm; P/N 044076, Dionex) equipped with an IonPac AG 11 50×4 mm I.D. precolumn (particle size 13 μm; PIN 044078, Dionex). Additionally, an anion trap column ATC-1 (PIN 037151, Dionex) was installed between the gradient pump and the injection valve. In order to minimize the baseline shift and to lower the background conductivity the ASRS-I suppresser working at 300 mA was installed. The range of the detector was set to 10 μS. The autosampler was cooled at 14° C., but the analysis itself was performed at room temperature. The mobile phase was composed of 100 mM NaOH (A) and deionized and degassed water (B). With that system the following gradient was produced:

| Time (min) | A (%) | B (%) |
|---|---|---|
| 0 | 1 | 99 |
| 25 | 1 | 99 |
| 14 | 23 | 77 |
| 18 | 60 | 40 |
| 24 | 60 | 40 |
| 26 | 1 | 99 |
| 45 | 1 | 99 |

The flow rate was 1 ml/min; run time was 45 min 1.4. Standards and Quality Control Samples A standard stock solution was prepared by dissolving 1 mg L-DHO in 1 ml water. Aliquots of 400 μl were frozen at −20° C. Stability of these solutions was guaranteed for at least 4 weeks. Defined amounts of the stock solution were added to the cell lysates and to human or rat serum and assayed to evaluate the linearity between the increase of the signal and the spiked L-DHO concentration. The precision and the accuracy of the method were investigated by using quality control (QC) samples with an L-DHO content in the low, the middle and the high concentration range of the signal/concentration linearity curve.

1.5. Sample Preparations 1.5.1. Cells

Jurkat cells were obtained by ATCC (TIB 182) and cultured as described in 1.5.1.1.

1.5.1.1 Tissue Culture Conditions

Jurkat cells were seeded at 5×10$^5$ ml and grown for 24 hours in RPMI 1640 medium and 10% fetal calf serum (FCS). Cells were pooled in fresh medium for cell lysis and the amount of cells and percentage of dead cells calculated by vital microscopy with Eosin. After 24 hours cell numbers had increased by 1.6–1.8 times with less than 7% dead cells. Jurkat cells taken for L-DHO determination had a proliferation ratio of 1.6–1.8 times in 24 hours and less than 7% dead cells.

1.5.1.2 Preparation of Cell Lysates

Cells were suspended in a defined medium volume and cell density of samples was determined via vital microscopy using Eosin. About $10 \times 10^6$ cells were removed, pelleted by 5 minute-centrifugation at 350×g and the supernatant was discarded. Lysis of the cells was done by resuspending the cell pellet in 500 µl 1.2 M $HClO_4$. This mixture was transferred in 2.0 ml Eppendorf safe-lock caps and the protein was precipitated by 2 minutes high speed centrifugation. The supernatant was completely removed, transferred in glass vials and after addition of 500 µl chloroform thoroughly mixed by 2 minutes vortexing. Cellular lipids were extracted by chloroform following 10 minutes centrifugation (1502 g) at 10° C. The purified supernatant was collected in 2 ml Eppendorf-caps and stored at −20° C. until further used. For the HPLC analysis 100 µl of this supernatant were neutralized with 30 µl 6 M KOH. After shaking for about 5 sec the samples were stored on ice for 30 min. Thereafter they were centrifuged for 5 min at 15 000 rpm. From the clear supernatant 20 µl were used for the HPLC analysis.

1.5.2. Serum

In order to reduce the protein content 200 pi serum were added to a Microcon filter (10 000 D, model 10, code 42407, Amicon) and centrifuged for 30 min at 13 000 rounds per minute (rpm). The flow through consisted of about 150 µl and contains the analyte L-DHO. From this liquid 20 µl were used for HPLC analysis.

1.6. Quantification

The integrator determined the peak-height of the analyte. Calibration curves were obtained by plotting the measured peak heights (y) vs the analyte concentration in the different biological matrices. Weighted linear regression (1/y) was used to back calculate the L-DHO concentration in standard samples as well as in quality controls. The common correlation coefficient R was provided by PROC GLM based on an analysis of the covariance model using the weighting factor.

1.7. Stability

Table 1 shows the stability data of the analyte at −20° C. in cell lysates and serum samples after 2–3 freezing/thawing cycles of one sample. L-DHO was stable under the above mentioned conditions in Jurkat cells over a period of at least 4 weeks. The detected increase in the concentration of some rat serum samples and one human serum sample after several thawing cycles of more than 10% cannot be explained and shows that the accuracy in such cases can be reduced up to 15% in general and up to 29% at the worst. For these reasons it can be stated only that in rat and human serum samples L-DHO is definitely stable only for at least 1 week.

TABLE 1

Stability data in cell lysates and serum at −20° C. (n = 1)

| Time (days) | concentration 1 20 µg/ml | Residue (%) | Concentration 2 100 µg/ml | Residue (%) |
|---|---|---|---|---|
| | | Jurkat cells | | |
| 0 | 19.34 | 100 | 100.05 | 100 |
| 7 | 19.28 | 99.7 | 99.09 | 99.0 |
| 14 | n.d. | n.d. | 115.32 | 115.3 |
| 29 | 19.98 | 103.3 | 99.35 | 99.3 |

| Time (h) | concentration 1 5 µg/ml | Residue (%) | Concentration 2 20 µg/ml | Residue (%) |
|---|---|---|---|---|
| | | Rat serum | | |
| 0 | 4.30 | 100 | 19.94 | 100 |
| 7 | 4.52 | 105.1 | 19.62 | 98.4 |
| 14 | 4.81 | 111.9 | 20.93 | 105.0 |
| 21 | 5.55 | 129.1 | 22.33 | 112.2 |
| | | Human serum | | |
| 0 | 4.67 | 100 | 20.22 | 100 |
| 8 | 4.81 | 103.0 | 20.38 | 100.8 |
| 65 | 4.87 | 104.3 | 23.20 | 114.7 |

Residue (%) is a percentage of concentration compared with the initial analysis.
n.d. = not determined In order to simulate the conditions of the samples when they are waiting in the autosampler for the actual analysis the stability during 18 h at 14° C. was determined. For that reason the cell lysates were spiked and then treated with 30 µl 6 M KOH/100 µl lysate before the start of the analysis. Correspondingly, the serum samples were spiked and then deproteinized as described in 1.5.2. As can be seen in Table 2 the L-DHO content is slightly reduced in cells under these conditions up to a maximum of about 7%. In serum samples the analyte is stable under these conditions. For these reasons only so many HPLC samples were prepared that the maximal length of stay in the autosampler was less than 18 h.

TABLE 2

Stability for 18 h at 14° C. (n = 1)

| Time (h) | concentration 1 20 µg/ml | Residue (%) | Concentration 2 100 µg/ml | Residue (%) |
|---|---|---|---|---|
| | | Jurkat cells | | |
| 0 | 19.96 | 100 | 100.02 | 100 |
| 18 | 18.60 | 93.2 | 97.43 | 97.4 |

| Time (h) | concentration 1 5 µg/ml | Residue (%) | Concentration 2 20 µg/ml | Residue (%) |
|---|---|---|---|---|
| | | Rat serum | | |
| 0 | 4.61 | 00 | 19.99 | 100 |
| 18 | 4.96 | 107.6 | 20.53 | 102.7 |
| | | Human serum | | |
| 0 | 3.34 | 100 | 18.78 | 100 |
| 18 | 3.37 | 100.9 | 22.09 | 117.6 |

1.8 Selectivity

The comparison of the unspiked Jurkat cell lysates with the corresponding chromatograms using cell lysates spiked with 50 µg L-DHO/ml showed that there is a little peak at 11.983 min, which is the same retention time as L-DHO. It is highly probable that this peak results from the natural content of the analyte in these cells. Additionally, it can be seen that due to the treatment of the cell lysates with KOH the L-DHO peak splits into two peaks. The KOH treatment however is essential in order to neutralize the acidic cell lysate prior to HPLC analysis. It could be shown that under the conditions described the evaluation of the second peak height (retention tim (RT)=11.954 min) can be used to get improved results in terms of linearity and reproducibility.

Also in the case of rat and human serum was found a blank value with the same retention time as L-DHO. It is supposed that this reflects the natural L-DHO content of the organism. Determination of at least 10 different samples of both species shows that the natural L-DHO content was below the detection limit of 1 µg/ml.

1.9 Linearity

The linearity of the determination was evaluated on five calibration curves for the cell line and the different serum samples. Samples were prepared and run on five different days with L-DHO concentrations in the range of 1.5–150 µg/ml (cell lysates) and 1–30 µg/ml (serum samples). The results are shown in Tables 3–5. For the determination of the regression line the peak height were used. Based on that the corresponding concentrations of the different standards were back calculated as indicated in the different tables.

TABLE 3

Linearity of L-DHO determinations in Jurkat cell lysates.
After spiking the samples were treated with 30 µl 6M KOH
and then analyzed once as described in 1.3.

| day | concentration (µg/ml) | | | | | | slope | y-intercept | r |
| --- | --- | --- | --- | --- | --- | --- | --- | --- | --- |
|     | 1.5 | 6 | 10 | 50 | 100 | 150 | | | |
| 1 | 1.78 | 5.54 | 9.09 | 49.80 | 102.46 | 149.09 | 1317.54 | −258.17 | 0.9995 |
| 2 | 1.90 | 5.14 | 9.54 | 50.77 | 100.22 | 150.20 | 1324.84 | 204.79 | 0.9995 |
| 3 | 1.86 | 5.24 | 9.46 | 51.18 | 99.91 | 150.07 | 1295.48 | 302.48 | 0.9996 |
| 4 | 1.85 | 5.34 | 9.39 | 51.45 | 100.97 | 148.71 | 1306.08 | 833.68 | 0.9996 |
| 5 | 1.86 | 5.26 | 9.53 | 50.98 | 100.07 | n.d. | 1318.67 | 530.19 | 0.9993 |
| Mean | 1.85 | 5.30 | 9.40 | 50.80 | 100.73 | 149.52 | 1312.52 | 322.59 | |
| S.D. | 0.04 | 0.15 | 0.19 | 0.63 | 1.05 | 0.73 | 11.69 | 404.93 | |
| C.V. (%) | 2.3 | 2.8 | 2.0 | 1.2 | 1.0 | 0.5 | 0.9 | 125.5 | |

R = 0.9995

TABLE 4

Linearity of L-DHO determinations in rat serum.
After spiking the serum was cleared from proteins as described in 1.5.2.

| day | concentration (µg/ml) | | | | | slope | y-intercept | r |
| --- | --- | --- | --- | --- | --- | --- | --- | --- |
|     | 1 | 5 | 10 | 20 | 30 | | | |
| 1 | 1.05 | 4.48 | 10.10 | 22.10 | 28.61 | 15334 | −4719.83 | 0.9966 |
| 2 | 1.16 | 4.59 | 8.60 | 21.07 | 30.97 | 17559 | −4630.68 | 0,9960 |
| 3 | 1.07 | 4.64 | 9.81 | 20.07 | 30.45 | 17674 | −3175.63 | 0.9995 |
| 4 | 1.11 | 4.62 | 9.54 | 19.27 | 31.65 | 18322 | −4296.53 | 0.9981 |
| 5 | 1.06 | 4.81 | 9.99 | 18.89 | 31.40 | 17738 | −829.00 | 0.9985 |
| Mean | 1.09 | 4.63 | 9.61 | 20.28 | 30.62 | 17325.40 | −3530.33 | |
| S.D. | 0.05 | 0.12 | 0.60 | 1.32 | 1.21 | 1151.65 | 1630.62 | |
| C.V. (%) | 4.2 | 2.6 | 6.3 | 6.5 | 4.0 | 6.7 | 46.19 | |

R = 0.9959

TABLE 5

Linearity of L-DHO determinations in human serum.
After spiking the serum was cleared from proteins as described in 1.5.2.

| day | concentration (µg/ml) | | | | | slope | y-intercept | r |
| --- | --- | --- | --- | --- | --- | --- | --- | --- |
|     | 1 | 5 | 10 | 20 | 30 | | | |
| 1 | 0.90 | 5.17 | 11.30 | 19.41 | 29.42 | 13498 | 2930.30 | 0.9980 |
| 2 | 0.99 | 4.87 | 10.12 | 21.51 | 28.68 | 15663 | 477.61 | 0.9982 |
| 3 | 0.94 | 4.94 | 11.29 | 19.41 | 29.59 | 14328 | 1367.80 | 0.9982 |
| 4 | 1.01 | 4.77 | 10.32 | 20.82 | 29.15 | 15777 | 1771.98 | 0.9992 |
| 5 | 1.01 | 4.81 | 10.10 | 20.86 | 29.28 | 15216 | 1612.77 | 0.9993 |
| Mean | 0.97 | 4.91 | 10.62 | 20.40 | 29.23 | 14896.4 | 1632.09 | |
| S.D. | 0.05 | 0.16 | 0.61 | 0.95 | 0.35 | 96746 | 881.47 | |
| C.V. (%) | 5.2 | 3.2 | 5.8 | 4.6 | 1.2 | 6.5 | 54.01 | |

R = 0.9986
*standard concentration (µg/ml)
— not determined

As can be seen in these tables the linearity in each case was proven. This is reflected in the individual correlation coefficients "r" which are in all cases >0.99. The mean linear regression line for the concentration curves obtained on 5 different days are described in each table and show that the slope was very well reproducible with a maximal variation of 6.7%.

The back calculated standard concentrations exhibited in the average a C.V. of less than 6.5% showing the high accuracy of the values. The common correlation value R of higher than 0.99 expresses the very high precision and reproducibility of the method.

1.10. Limit of Quantification

Based on these results the limit of quantification in Jurkat cells is 1.5 μg/ml. In rat and human serum samples 1 μg/ml L-DHO can be detected. Spiked samples at these concentration showed a signal to noise ratio of at least 1:3.

1.12. Accuracy and Precision

The accuracy and precision of replicate determinations of L-DHO at three different concentrations on five different days are summarized in tables 6–8. Accuracy is expressed as the % difference of found to added amount of L-DHO (recovery). The intra day precision expressed as C.V. (%) was calculated using the two values that were obtained when one sample was measured twice on one day. The inter day precision was also expressed as C.V. (%) and was calculated using the mean found values of each control sample on 5 different days.

TABLE 6

Accuracy and Precision in Jurkat cell lysates after spiking and subsequent neutralization with 30 μl 6M KOH. n = means that one cell lysate sample was spiked with the corresponding concentration and measured twice.

| control sample (μg/ml) | Day | n | Accuracy Mean found (μg/ml) | recovery (%) | Precision C.V. (%) intra day | C.V. (%) inter day |
|---|---|---|---|---|---|---|
| 20 | 1 | 2 | 20.10 | +0.5 | 1.4 | 2.9 |
|  | 2 | 2 | 19.20 | −4.0 | 1.3 |  |
|  | 3 | 2 | 19.40 | −2.8 | 3.9 |  |
|  | 4 | 2 | 19.51 | −2.5 | 2.2 |  |
|  | 5 | 2 | 18.55 | −7.2 | 1.3 |  |
| 70 | 1 | 2 | 69.12 | −1.3 | 0.1 | 2.8 |
|  | 2 | 2 | 69.13 | −1.2 | 0.8 |  |
|  | 3 | 2 | 73.69 | +5.3 | 0.2 |  |
|  | 4 | 2 | 71.52 | +2.2 | 1.1 |  |
|  | 5 | 2 | 69.64 | −0.5 | 0.9 |  |
| 130 | 1 | 2 | 123.21 | −5.2 | 2.8 | 6.0 |
|  | 2 | 2 | 114.78 | −11.7 | 12.0 |  |
|  | 3 | 2 | 135.21 | +4.0 | 0.2 |  |
|  | 4 | 2 | 126.89 | −2.4 | 1.4 |  |
|  | 5 | 2 | 122.43 | −5.8 | 4.1 |  |

TABLE 7

Accuracy and Precision in rat serum after spiking and subsequent deproteinisation; n = 2 means that one serum sample was spiked with the corresponding concentration and measured twice.

| control sample (μg/ml) | Day | n | Accuracy Mean found (μg/ml) | recovery (%) | Precision C.V. (%) intra day | C.V. (%) inter day |
|---|---|---|---|---|---|---|
| 8 | 1 | 2 | 7.68 | −4.0 | 0.4 | 3.0 |
|  | 2 | 2 | 7.73 | −3.4 | 1.0 |  |
|  | 3 | 2 | 7.83 | −2.2 | 2.1 |  |
|  | 4 | 2 | 7.43 | −7.1 | 1.0 |  |
|  | 5 | 2 | 8.06 | +0.7 | 0.6 |  |
| 15 | 1 | 2 | 14.53 | −3.1 | 6.8 | 1.8 |
|  | 2 | 2 | 14.73 | −1.8 | 1.3 |  |
|  | 3 | 2 | 14.26 | −5.0 | 0.1 |  |
|  | 4 | 2 | 14.85 | −1.0 | 0.4 |  |
|  | 5 | 2 | 14.88 | −0.8 | 0.9 |  |
| 25 | 1 | 2 | 24.98 | −0.1 | 2.5 | 3.7 |
|  | 2 | 2 | 25.83 | +3.3 | 1.3 |  |
|  | 3 | 2 | 25.43 | +1.7 | 0.6 |  |
|  | 4 | 2 | 24.31 | −2.8 | 2.0 |  |
|  | 5 | 2 | 26.81 | +7.2 | 0.2 |  |

TABLE 8

Accuracy and Precision in human serum after spiking and subsequent proteinization; n = 2 means that one serum sample was spiked with the corresponding concentration and measured twice.

| control sample (μg/ml) | Day | n | Accuracy Mean found (μg/ml) | recovery (%) | Precision C.V. (%) intra day | C.V. (%) inter day |
|---|---|---|---|---|---|---|
| 8 | 1 | 2 | 7.77 | −2.9 | 0.7 | 3.8 |
|  | 2 | 2 | 7.84 | −2.0 | 15.5 |  |
|  | 3 | 2 | 7.43 | −7.1 | 10.9 |  |
|  | 4 | 2 | 7.17 | −10.4 | 2.1 |  |
|  | 5 | 2 | 7.80 | −2.5 | 1.2 |  |
| 15 | 1 | 2 | 13.88 | −7.5 | 0.9 | 6.0 |
|  | 2 | 2 | 14.00 | −6.7 | 8.5 |  |
|  | 3 | 2 | 15.10 | +0.6 | 1.5 |  |
|  | 4 | 2 | 15.13 | +0.8 | 7.2 |  |
|  | 5 | 2 | 16.03 | +6.8 | 12.8 |  |
| 25 | 1 | 2 | 26.56 | +6.2 | 3.4 | 4.2 |
|  | 2 | 2 | 23.77 | −4.9 | 0.7 |  |
|  | 3 | 2 | 24.80 | −0.8 | 4.7 |  |
|  | 4 | 2 | 25.46 | +1.8 | 7.8 |  |
|  | 5 | 2 | 24.54 | −1.9 | 0.2 |  |

The results presented here show that in most cases the control values were found with +/−10% variation at a maximum and that the method therefore is very accurate. Only in one case the recovery in Jurkat cell determinations differed slightly from that value (31 11.7%). This effect can be explained by the high intra day variation of 12%. The intra day precision in Jurkat cells, rat or human serum was lower than 5%, 7% and 10% respectively. The inter day precision in all matrices investigated was very low with a C.V. of less than 6.0%. This shows that the results obtained are highly reproducible and precise.

EXAMPLE 2

2.1. Tissue Culture Conditions

Preparation of serum free medium: Iscove powdered medium (Biochrom) was dissolved in 10 liters bidestilled water supplemented with 18.95.g NaCl, 11.43 g $NaHCO_3$, 700 mg KCl, 10 ml 35% NaOH solution, and 0.5 ml 1 M mercaptoethanol solution (Riedel de Haen) and sterile filtered. To one liter prepared Iscove medium 32 mg human holo-transferrin, 1 g bovine albumin and 1.5 ml lipids (Sigma) were added before use.

Cell Culture: A20.2.J cells were cultured in serum free medium (37° C., 5% $CO_2$) in an expansion culture at logarithmic cell growth. Cells taken for assays had a 2.2 fold proliferation rate in 24 h. The percentage of dead cells were <8% (3).

Treatment of cell with N-(4-trifluoromethyl)-2-cyano-3-hydroxy-crotonamide prepared as described in EP-0 529 500, hereinafter A 77 1726. A77 1726 was dissolved in aqua bidest (10 mM) and further diluted in serum free medium. Cells were then given the appropriate amount of A77 1726 and incubated at 37° C. and 5% $CO_2$.

2.2. Preparation of Cell-lysates for DHO Determination

Prepared cells were resuspended in a defined medium volume and cell density. Depending on expected DHO content, between 1–50 million cells were removed, pelleted (5 min, 350×g) and supernatant discarded. Cell were lysed, by adding 500 µl 1.2 M $HClO_4$. The lysates were transferred into 2 ml Eppendorf safe-lock-caps, and the protein precipitated by 2 min high speed centrifugation. The acidified lysates were completely removed, transferred into glass vials and, after addition of 500 µl chloroform, thoroughly mixed by 2 min vortexing. Cellular lipids were extracted following 10 min cold centrifugation (1502×g; 10° C.). The purified supernatants were collected in 2 ml Eppendorf caps for storage at −20° C. until high pressure liquid chromatography (HPLC) determination.

2.3 HPLC Determination of DHO

The chromatographic separation was performed as described in example 1. The range of the conductive detector was set to 10 µS. The analysis was performed at room temperature. The mobile phase was composed of 100 mM NaOH (A) and water (B). With that system the following gradient was produced:

| Time (min) | A (%) | B (%) |
| --- | --- | --- |
| 0 | 1 | 99 |
| 2.5 | 1 | 99 |
| 14 | 8 | 92 |
| 22 | 8 | 92 |
| 28 | 60 | 40 |
| 32 | 60 | 40 |
| 34 | 1 | 99 |
| 49 | 1 | 99 |

The flow rate was 1 ml/min; run time was 49 min 2.4 Results

A20.2J cells incubated with A77 1726 had increased amounts of intracellular DHO (TAbles 9–11). The results depicted in Table 9 demonstrate that DHO-levels directly correlated with the number of extracted cells.

TABLE 9

Correlation of Intracellular DHO-Concentrations and Number of Cells Cultured with A77 1726

| Cells (×10⁶) | DHO-Concentration (µg/ml ± SD) | |
| --- | --- | --- |
| | Experiment 1 (E10 B) | Experiment 2 (E14) |
| 1 | 14.08 ± 2.40 | 11.75 ± 0.23 |
| 2 | 19.51 ± 6.47 | 28.27 ± 0.79 |
| 4 | 53.58 ± 3.50 | 57.20 ± 2.76 |
| 6 | 73.01 ± 1.49 | 85.38 ± 2.33 |
| 8 | 99.89 ± 5.96 | 107.02 ± 3.47 |
| 10 | 113.37 ± 4.24 | 128.73 ± 1.95 |

A20.2.J cells were treated with 5 µM A77 1726 and cultured for 24 hours (37° C., 5% $CO_2$) and then prepared for DHO extraction (n=3).

To optimize cell culture methods and determine the best cell/A77 1726 molarity ratio, varying densities of A20.2.J cells were incubated together with A77 1726 (5 µM). Samples were withdrawn at different time points and DHO-concentrations determined (Table 10). Due to the fact that DHO-concentrations directly correlated with the amount of extracted cells (see Table 9), for the following experiments DHO-concenrations were extrapolated to 10×10⁶ cells in µg/ml. The best linear increase of DHO-level was found at a density of 1×10⁶ cells/ml. Using this cell density, the time dependent increase of intracellular DHO-levels in cells incubated with A77 1726 was studied. Detectable amounts of DHO could be determined after 1 hour of incubation, independent of the drug concentration (Table 11). A linear increase was registered with the greatest amount of DHO determined after 6 h (Table 11). After this time period a saturation was observed with no further increase of DHO.

TABLE 10

Cell density and time dependent increase of intracellular DHO-concentrations

| Incubation | Concentration | DHO (µg/ml) mean ± SD | |
| --- | --- | --- | --- |
| time (h) | 1 × 10⁶ cells/ml | 2 × 10⁶ cells/ml | 3 × 10⁶ cells/ml |
| 1 | 6.25 ± 0.42 | 5.47 ± 0.10 | 5.63 ± 0.19 |
| 4 | 33.06 ± 2.26 | 26.36 ± 0.42 | 19.39 ± 1.87 |
| 7 | 60.07 ± 0.01 | 42.31 ± 1.07 | 28.79 ± 0.34 |

Various amounts of A20.2.J-cells were incubated together with A77 1726 (5 µM), for the time periods given above, and their intracellular DHO-concentrations determined for each sample point. (* all values extrapolated to 10×10⁶ cells) (n=2).

TABLE 11

Time dependent increase of intracellular L-DHO-concentrations

| Incubation | Concentration DHO (µg/ml) mean ± SD | | |
| --- | --- | --- | --- |
| time (h) | A77 1726 (5 µM) | A77 1726 (10 µM) | A77 1726 (25 µM) |
| 0 | 2.73 ± 0.10 | 2.73 ± 0.10 | 2.73 ± 0.08 |
| 1 | 9.20 ± 0.09 | 8.5 ± 0.39 | 15.05 ± 0.26 |
| 2 | 24.03 ± 1.15 | 20.74 ± 1.43 | 26.06 ± 0.20 |
| 4 | 59.48 ± 0.72 | 58.65 ± 2.06 | 50.21 ± 1.54 |
| 7 | 87.54 ± 1.58 | 82.65 ± 4.50 | 114.89 ± 3.61 |

One million A20.2.J-cells/ml were incubated together with varying concentrations of A77 1726 and their intracellular DHO-concentrations determined at different time points. The data are given as µg/ml DHO±SD extrapolated to ten million cells (0–4 h=n=2, 7 h=n=4).

Incubation of A20.2.J tumor cells with A77 1726, resulted in rapid accumulation of L-DHO due to DHO-DH inhibition. The intracellular L-DHO-concentrations correlated with cell number and were time dependent. L-DHO monitoring is a surrogate marker for A77 1726 immunomodulating activity in patients.

EXAMPLE 3

Animals: Male Wistar-Lewis rats (Mollegaard Breading Center Ltd. Ejby, DK) with a body weight of 160–200 g.

Adjuvant Arthritis: The disease was induced by injecting 0.1 ml Freund's adjuvant (6 mg *Mycobacterium smegmatis* suspended in 1 ml heavy, white paraffin oil (Merck, Darmstadt) into the root of Wistar-Lewis rat's tails. Pathological symptoms generally appear between 10 and 14 days after disease induction.

Drug Treatment: Drugs were suspended in 1% carboxymethylcellulose (COMC). Healthy animals (n=18) and adjuvant diseased (n=18) rats (day 9 of the disorder), were given 10 mg/kg, p.o. N-4-(trifluoromethylphenyl)-5-methylisoxazol-4-carboxamide, hereinafter leflunomide twice daily (7:30 h and 13:30 h) for 5 days, i.e. at time points: 0 h, 6 h, 24 h, 30 h, 48 h, 54 h, 72 h, 78 h, 96 h. (see table 12). At time point 0 h, 3 animals from both diseased and non-diseased groups were sacrificed to determine baseline levels. An additional 3 healthy and 3 diseased animals were treated with placebo (COMC alone) for 5 days.

Sampling: Three animals per group were sacrificed at each sampling time point. Serum and splenocytes taken at 3 h, 7 h, 27 h, 51 h, 75 h, and 99 h (see table 12). With the exception of the 7 h value, samples were taken three hours after the last drug application. The 7 h value was taken one hour after the second dosing. Samples from the placebo treated animals were taken at the 0 h (n=3) and 99 h (n=3) time points (400 µl) added and mixed. The HPLC conditions were as follows: The hardware consisted of a TSP P2000 pump, a TSP AS1000 auto-sampler, a TSP SP4270 integrator, and a TSP UV100 UV-detector. Detection was at 292 nm wavelength. The mobile phase consisted of 650 ml methanol (CHROMASOLV), 2,42 g tetrabutylammoniumbromide, and 350 ml 0,05 M Ammoniumacetate. The flow rate was 0.5 ml/min A CHROMPACK Spherisorb ODS-2 10 cm column with a 1 cm reversed phase (R2) guard column was used. 100 µl was injected into the column and the running time was 7 min.

HPLC determination of L-DHO-concentrations: The chromatographic separation was performed as described in example 1. The range of the conductivity detector was set to 10 µS; the analysis was performed at room temperature. The mobile phase was composed of 100 mM NaOH (A) and water (B). With that system the following gradients were produced:

TABLE 12

Administration of leflunomide and tissue sampling times

| Hour: | 0 | 3 | 6 | 7 | 24 | 27 | 30 | 48 | 51 | 54 | 72 | 75 | 78 | 96 | 99 |
|---|---|---|---|---|---|---|---|---|---|---|---|---|---|---|---|
| Drug (p.o.) | ↑ | | ↑ | | ↑ | | ↑ | ↑ | | ↑ | ↑ | | ↑ | ↑ | |
| Sampling | ↑ | ↑ | | ↑ | | ↑ | | | ↑ | | | ↑ | | | ↑ |

Preparation of Samples:

Blood collected by heart puncture was stored for 30 min at 4° C. and then centrifuged for 10 min at 3000 rpm. Serum was separated and stored in Eppendorf-caps at −20° C. (3). Before HPLC analysis, the frozen serum was thawed and, in order to remove the proteins, 200 µl serum were added to a Microcon filter (model 10, code 42407, Amicon) and centrifuged for 30 min at 13 000 rpm.

Spleens were taken (n=3) and pooled for L-DHO analysis. Cells separated by teasing (passing through a stainless steel strainer) were treated with 0.17 M NH$_4$Cl, to lyse the erythrocytes. Aliquots of 50 million spleen cells per group were prepared, placed in caps for centrifugation and supernatant discarded. The cell pellet was, under permanent mixing, given 500 µL of a 1.2 M HClO$_4$ solution to lyse the cells and centrifuged for 2 min The acidic cell lysate was completely transferred to glass vials, 500 µl chloroform added and mixed for 2 min with a Vortex mixer. Cellular lipids were precipitated by centrifugation (10 min 1502×g and 10° C.). The supernatant was placed in 2 ml caps and stored at −20° C.

Determination of A77 1726 serum concentrations was conducted as follows: serum samples were brought to room temperature and thoroughly mixed using a vortex mixer. The serum was pipetted (200 µl) in Eppendorf caps and the internal standard (A 77 1726, 2 µg in 400 µl acetonitril) added. The tubes were then mixed in a Vortex mixer and centrifuged at 2500 rpm (room temperature) for 10 minutes. For HPLC analysis, the supernatant (400 µl) was transferred to a vial and water

| Serum | | |
|---|---|---|
| Time (min) | A (%) | B (%) |
| 0 | 1 | 99 |
| 2.5 | 1 | 99 |
| 14 | 23 | 77 |
| 18 | 60 | 40 |
| 24 | 60 | 40 |
| 26 | 1 | 99 |
| 45 | 1 | 99 |

| Splenocytes | | |
|---|---|---|
| Time (min) | A (%) | B (%) |
| 0 | 1 | 99 |
| 2.5 | 1 | 99 |
| 14 | 8 | 92 |
| 22 | 8 | 92 |
| 28 | 60 | 40 |
| 32 | 60 | 40 |
| 34 | 1 | 99 |
| 49 | 1 | 99 |

The flow rate was 1 ml/min

Both healthy and diseased rats had increased cellular (Table 13) and serum (Table 14) L-DHO concentrations after oral administration of leflunomide. This increase correlated with the A77 1727 serum concentrations determined in these animals (Table 15). Initially, 3 hours after oral drug administration, A77 1726 reached a concentration of about 26 µg/ml in adjuvant diseased rats and 31 µg/ml in non-diseased rats. These values peaked one hour after the second dosing (7 h), but dropped to values between 7 to 12 μg/ml for the duration of the experiment in both diseased and non-diseased rats. Diseased animals took 51 h to reach these concentrations, whereas non-diseased rats already had reached them after 27 h (Table 15). The A77 1726 serum concentrations correlated with the L-DHO-concentrations in the serum of adjuvant diseased and non-diseased rodents. Contrary to the L-DHO-serum concentrations, which equilibrated to about 5 μg/ml for duration of experiment, the amount of L-DHO found in the splenocytes fell below the detection limit (1.5 μg/ml) after 99 h.

TABLE 13

L-DHO-concentrations in splenocytes [50 × 10$^6$ cells] from rats treated with Leflunomide

| | | Adjuvant Diseased Rats | | | | Non-Diseased Rats | | |
|---|---|---|---|---|---|---|---|---|
| Time [Hours] | Single Value | Mean [μg/ml] | SD [μg/ml] | SD [%] | Single Value | Mean [mg/ml] | SD [μg/ml] | SD [%] |
| 0 (Placebo) | <D.L. <D.L. | <D.L. | | | <D.L. <D.L. | <D.L. | | |
| 3 | 5.81 4.60 | 5.21 | 0.60 | 11.52 | 5.09 6.31 | 5.70 | 0.61 | 10.70 |
| 7 | 13.00 11.22 | 12.11 | 0.89 | 7.35 | 16.77 14.87 | 15.82 | 0.95 | 6.01 |
| 27 | 16.28 16.84 | 16.56 | 0.28 | 1.69 | 8.69 10.25 | 9.47 | 0.78 | 8.24 |
| 51 | 3.63 3.97 | 3.80 | 0.17 | 4.47 | 1.84 2.34 | 2.09 | 0.25 | 11.96 |
| 75 | 2.58 2.71 | 2.65 | 0.06 | 2.26 | 1.92 2.24 | 2.08 | 0.16 | 7.69 |
| 99 | <D.L. <D.L. | <D.L. | | | <D.L. <D.L. | <D.L. | | |
| Placebo (99) | <D.L. <D.L. | <D.L. | | | <D.L. <D.L. | <D.L. | | |

Animals were treated with leflunomide or placebo, spleens removed (n=3) and as described. The pooled splenocytes were assayed in duplicate. DL=n limit (1.5 μg/ml);

TABLE 14

L-DHO-concentrations in serum from rats treated with leflunomide

| | | | Adjuvant Diseased Rats | | | | Non-Diseased Rats | | |
|---|---|---|---|---|---|---|---|---|---|
| Time [Hours] | Rat | Single Value | Mean [μg/ml] | SD [μg/ml] | SD [%] | Single Value | Mean [mg/ml] | SD [μg/ml] | SD [%] |
| 0 (Placebo) | 1 | <D.L. | <D.L. | | | <D.L. | <D.L. | | |
| | 2 | <D.L. | | | | <D.L. | | | |
| | 3 | <D.L. | | | | <D.L. | | | |
| 3 | 1 | 7.85 | 8.52 | 0.99 | 11.70 | 11.92 | 11.13 | 0.67 | 6.30 |
| | 2 | 9.66 | | | | 10.88 | | | |
| | 3 | 8.05 | | | | 10.60 | | | |
| 7 | 1 | 19.55 | 17.54 | 1.81 | 10.30 | 20.29 | 18.66 | 1.45 | 7.80 |
| | 2 | 17.00 | | | | 18.14 | | | |
| | 3 | 16.06 | | | | 17.54 | | | |
| 27 | 1 | 19.73 | 16.45 | 3.06 | 18.60 | 8.22 | 8.43 | 0.21 | 2.50 |
| | 2 | 15.95 | | | | 8.42 | | | |
| | 3 | 13.67 | | | | 8.64 | | | |
| 51 | 1 | 3.06 | 3.27 | 0.36 | 11.00 | 4.87 | 4.55 | 0.46 | 10.20 |
| | 2 | 3.68 | | | | 4.77 | | | |
| | 3 | 3.06 | | | | 4.02 | | | |
| 75 | 1 | 5.38 | 5.14 | 0.61 | 11.90 | 4.60 | 4.33 | 0.23 | 5.40 |
| | 2 | 4.45 | | | | 4.17 | | | |
| | 3 | 5.60 | | | | 4.23 | | | |
| 99 | 1 | 5.48 | 5.02 | 0.41 | 8.30 | 5.67 | 5.75 | 0.85 | 14.80 |
| | 2 | 4.89 | | | | 6.64 | | | |
| | 3 | 4.68 | | | | 4.95 | | | |
| Placebo (99) | 1 | <D.L | <D.L. | | | <D.L | D.L | | |
| | 2 | <D.L | | | | <D.L | | | |
| | 3 | <D.L | | | | <D.L | | | |

Animals were treated with leflunomide or placebo and blood taken, prepared and assayed as described. L-DHO serum concentrations were determined for each animal individually. DL=detection limit (0.5 µg/ml);

TABLE 15

A77 1726 concentrations in serum from rats treated with leflunomide

| Time [Hours] | Rat | Adjuvant Diseased Rats | | | | Non-Diseased Rats | | | |
|---|---|---|---|---|---|---|---|---|---|
| | | Single Value | Mean [µg/ml] | SD [µg/ml] | SD [%] | Single Value | Mean [mg/ml] | SD [µg/ml] | SD [%] |
| 0 (Placebo) | 1 | 0.0 | 0.0 | 0.0 | | 0.0 | 0.0 | 0.0 | |
| | 2 | 0.0 | | | | 0.0 | | | |
| | 3 | 0.0 | | | | 0.0 | | | |
| 3 | 1 | 26.8 | 26.33 | 1.17 | 4.45 | 32.0 | 30.7 | 1.21 | 3.92 |
| | 2 | 27.2 | | | | 30.6 | | | |
| | 3 | 25.0 | | | | 29.6 | | | |
| 7 | 1 | 44.1 | 42.3 | 4.11 | 9.71 | 47.7 | 47.9 | 1.46 | 3.04 |
| | 2 | 45.2 | | | | 49.4 | | | |
| | 3 | 37.6 | | | | 46.5 | | | |
| 27 | 1 | 21.3 | 19.7 | 3.34 | 16.92 | 10.2 | 9.6 | 0.74 | 7.65 |
| | 2 | 22.0 | | | | 9.9 | | | |
| | 3 | 15.9 | | | | 8.8 | | | |
| 51 | 1 | 9.1 | 9.2 | 1.00 | 10.93 | 7.8 | 7.4 | 1.48 | 19.97 |
| | 2 | 10.2 | | | | 8.7 | | | |
| | 3 | 8.2 | | | | 5.8 | | | |
| 75 | 1 | 9.0 | 9.9 | 3.09 | 31.34 | 6.7 | 8.1 | 1.35 | 16.70 |
| | 2 | 7.3 | | | | 9.4 | | | |
| | 3 | 13.3 | | | | 8.2 | | | |
| 99 | 1 | 12.0 | 12.2 | 0.38 | 3.11 | 14.6 | 12.7 | 1.67 | 13.08 |
| | 2 | 11.9 | | | | 11.4 | | | |
| | 3 | 12.6 | | | | 12.2 | | | |
| Placebo (99) | 1 | 0.0 | 0.0 | 0.0 | | 0.0 | 0.0 | 0.0 | |
| | 2 | 0.0 | | | | 0.0 | | | |
| | 3 | 0.0 | | | | 0.0 | | | |

Animals were treated with leflunomide or placebo and blood taken, prepared and assayed as described. A77 1726 serum concentrations were determined for each animal individually;

Orally apllied leflunomide is very fast converted to A77 1726 in vivo. A77 1726 is the active metabolite of leflunomide (U.S. Pat. No. 5,679,709). Incubation of either adjuvant diseased or non diseased rats with leflunomide resulted in rapid accumulation of L-DHO in their serum and splenocytes. L-DHO concentration correlated with blood serum concentrations of A77 1726, thus demonstrating the active suppression of DHO-DH through this molecule in vivo. In human clinical studies L-DHO monitoring can be a surrogate marker for leflunomide's immunomodulating activity in patients.

What is claimed is:

1. A chromatographic process for separating L-dihydroorotic acid from a sample comprising the steps of:
    a) loading a sample solution comprising L-dihydroorotic acid and interfering material onto a high pressure liquid chromatography column containing a quantity of pressure-stable anionic exchange material effective to bind essentially all of said L-dihydroorotic acid in said sample;
    b) eluting said column with an aqueous basic eluting solution having a base concentration effective to remove said interfering material from said anionic exchange material without removing said L-dihydroorotic acid, until essentially all of said interfering material has been removed from said column; and
    (c) eluting said column with an aqueous basic eluting solution having a base concentration effective to remove said L-dihydroorotic acid from said anionic exchange material, until essentially all of said L-dihydroorotic acid has been removed from said column essentially free of said interfering material, wherein the operating pressure of said column is from about 1.1 MPa to about 40 MPa.

2. The process according to claim 1, wherein the base is sodium hydroxide.

3. The process according to claim 1, wherein the pressure-stable anionic exchange material is selected from a divinylbenzene/ethylvinylbenzene polymer, a polyvinylbenzylammonium polymer cross-linked with divinylbenzene, or mixtures thereof, which are modified with alkanol quaternary ammonium.

4. The process according to claim 1, wherein the pressure is from about 4.1 MPa to about 5.5 MPa.

5. The process according to claim 1, wherein eluting by the aqueous basic eluting solution is accomplished by a time gradient of the base concentration.

6. The process according to claim 5, wherein the time gradient of the base concentration is linear.

7. The process as claimed in claim 1 further comprising detecting the L-dihydroorotic acid by a conductivity detector.

8. A diagnostic assay, comprising the process as claimed in claim 1.

9. The process as claimed in claim 1 further comprising determining the activity of a dihydroorotic acid dehydrogenase inhibitor.

10. The process as claimed in claim 9, wherein the dihydroorotic acid dehydrogenase inhibitor is at least one inhibitor selected from N-4-(trifluoromethylphenyl)-5-methylisoxazol-4-carboxamide, Brequinar, N-(4-trifluoromethylphenyl)-2-cyano-3-hydroxyhept-2-en-6-yne-carboxamide, 2-cyano-3-cyclopropyl-3-hydroxyacrylic-acid-(4-cyanophenyl)-amide and N-(4-trifluoromethylphenyl)-2-cyano-3-hydroxycrotonamide.

11. A chromatographic process for measuring the activity of a dihydroorotic acid dehydrogenase inhibitor, comprising the steps of:
  a) loading a sample solution comprising a dihydroorotic acid dehydrogenase inhibitor with dihydroorotic dehydrogenase activity which produces L-dihydroorotic acid, and interfering material onto a high pressure liquid chromatography column containing a quantity of pressure-stable anionic exchange material effective to bind essentially all of said L-dihydroorotic acid in said sample;
  b) eluting said column with an aqueous basic eluting solution including a base concentration effective to remove said interfering materials from said anionic exchange material without removing said L-dihydroorotic acid, until essentially all of said interfering material has been removed from said column;
  c) eluting said column with an aqueous basic eluting solution having a base concentration effective to remove said L-dihydroorotic acid from said anionic exchange medium, until essentially all of said L-dihydroorotic acid is removed from said column essentially free of said interfering material, wherein the operating pressure of said column is from about 1.1 MPa to about 40 MPa;
  d) measuring the concentration of said L-dihydroorotic acid; and
  e) determining the activity of the dihydroorotic acid dehydrogenase from the measured concentration of said L-dihydroorotic acid.

12. The process as claimed in claim 11, wherein the dihydroorotic acid dehydrogenase inhibitor is at least one inhibitor selected from N-4-(trifluoromethylphenyl)-5-methylisoxazol-4-carboxamide, Brequinar, N-(4-trifluoromethylphenyl)-2-cyano-3-hydroxyhept-2-en-6-yne-carboxamide, 2-cyano-3-cyclopropyl-3-hydroxyacrylic-acid-(4-cyanophenyl)-amide, and N-(4-trifluoromethylphenyl)-2-cyano-3-hydroxycrotonamide.

13. A diagnostic assay, comprising the process as claimed in claim 11.

* * * * *